United States Patent
Khan et al.

(10) Patent No.: US 9,649,508 B2
(45) Date of Patent: May 16, 2017

(54) METHODS, SYSTEMS AND COMPUTER READABLE STORAGE MEDIA STORING INSTRUCTIONS FOR DETERMINING PATIENT SPECIFIC TREATMENT PLANNING MARGINS

(71) Applicants: EMORY UNIVERSITY, Atlanta, GA (US); University of Tennessee Research Foundation, Knoxville, TN (US)

(72) Inventors: Mohammad Khurram Khan, Atlanta, GA (US); Michael Edward Howard, Ooltewah, TN (US); Laurence F. Miller, Knoxville, TN (US)

(73) Assignees: Emory University, Atlanta, GA (US); University of Tennessee Research Foundation, Knoxville, TN (US)

( * ) Notice: Subject to any disclaimer, the term of this patent is extended or adjusted under 35 U.S.C. 154(b) by 349 days.

(21) Appl. No.: 14/026,562

(22) Filed: Sep. 13, 2013

(65) Prior Publication Data

US 2014/0073833 A1    Mar. 13, 2014

Related U.S. Application Data

(60) Provisional application No. 61/700,480, filed on Sep. 13, 2012.

(51) Int. Cl.
*A61N 5/00* (2006.01)
*A61N 5/10* (2006.01)

(52) U.S. Cl.
CPC .................. *A61N 5/1037* (2013.01)

(58) Field of Classification Search
CPC .... A61N 5/103; A61N 5/1039; A61N 5/1045; A61N 2005/1041; A61N 2005/1074
(Continued)

(56) References Cited

U.S. PATENT DOCUMENTS 7,639,853 B2   12/2009   Olivera et al.
8,042,209 B2   10/2011   D'Souza et al.
(Continued)

FOREIGN PATENT DOCUMENTS

WO   2013024380 A1   2/2013
WO   2013117991 A1   8/2013

OTHER PUBLICATIONS

Herschtal et al. "Finding the optimal statistical model to describe target motion during radiotherapy delivery—a Bayesian approach" Physics in Medicine and Biology, 2012; 57(9): 2743-2755.
(Continued)

*Primary Examiner* — Samuel Gilbert
(74) *Attorney, Agent, or Firm* — Emory Patent Group

(57) ABSTRACT

Methods, systems and computer-readable storage media relate to determining individualized treatment planning margins. The methods may include processing motion data of a target obtained from at least one marker for one or more periods. Each period may include a plurality of time intervals. The processing may include processing the motion data to determine an isocenter for each time interval along at least one of the axes of motion. The axes can include the x axis, the y axis, and/or the z axis. The method may include determining motion prediction data for each of the at least one of the axes; and determining treatment planning margins for each of the at least one of the axes based on the motion prediction data. The individualized treatment margins can be smaller and more optimal because the treatment margins can incorporate patient specific patterns of motion of a target (e.g., an organ).

23 Claims, 7 Drawing Sheets

(58) Field of Classification Search
USPC .................................................. 600/1; 378/65
See application file for complete search history.

(56) References Cited

U.S. PATENT DOCUMENTS

| | | | |
|---|---|---|---|
| 8,095,203 B2 | 1/2012 | Wright et al. | |
| 8,244,330 B2 | 8/2012 | Meier et al. | |
| 8,379,794 B2 | 2/2013 | Poulsen et al. | |
| 8,437,449 B2 | 5/2013 | Riley et al. | |
| 8,467,497 B2 | 6/2013 | Lu et al. | |
| 2009/0257557 A1* | 10/2009 | Sumanaweera | A61N 5/1049 378/65 |
| 2010/0152600 A1 | 6/2010 | Droitcour et al. | |
| 2010/0266099 A1* | 10/2010 | Busch | A61N 5/1048 378/65 |
| 2012/0280135 A1* | 11/2012 | Bal | G06T 7/0083 250/395 |
| 2014/0005464 A1* | 1/2014 | Bharat | A61N 5/1031 600/1 |

OTHER PUBLICATIONS

Howard et al. "Individualized Predictive Treatment Margins to Account for Prostate Motion during Treatment using Real-time Intra-fraction Tracking," International Journal of Radiation Oncology, 2010. 78(3): p. S370-371.

Howard et al. "Individualized Predictive Treatment Margins to Account for Prostate Motion during Treatment using Real-time Intra-fraction Tracking" presented at 2010 ASTRO Annual Meeting, San Diego.

Howard "Development of Patient Specific Predictive Margins to Account for Prostate Motion During Treatment Using Real-Time Intra Fraction Tracking," Dec. 2012, retrieved from the Internet <URL: http:trace.tennessee.edu/cgi/viewcontent.cgi?article=2773 &context=utk_graddiss> on Mar. 10, 2016.

Kraub "Compensation of intra-fractional organ motion through multileaf collimator tracking," Feb. 1, 2012, retrieved from the Internet <URL: http://archiv.ub.uni-heidelberg.de/volltextserver/13118/1/krauss_dissertation.pdf> on Mar. 8, 2016.

Langen et al. "Observations on Real-Time Prostate Gland Motion Using Electromagnetic Tracking" International Journal of Radiation Biology Physics, 2008; 71(4): 1084-1090.

Li et al. "3D Bayesian Tracking with a Single Imager for Real-Time Image Guidance in Prostate Radiation Therapy" 2011 10th International Conference on Machine Learning and Applications, 2011: 210-214.

Litzenberg et al. "Prostate Intrafraction Translation Margins for Real-Time Monitoring and Correction Strategies" Prostate Cancer, 2012; (2012): 1-6.

Preiswerk et al. "A Bayesian Framework for Estimating Respiratory Liver Motion from Sparse Measurements" Abdominal Imaging, Computational and Clinical Applications, 2011, LNCS 7029, p. 207-214, Springer, London, New York, 2012.

Rassiah-Szegedi et al. "Individualized margins for prostate patients using a wireless localization and tracking system" Journal of Applied Clinical Medical Physics, 2011, 12(3): 194-204.

* cited by examiner

| Time (t) | Transponder (1,2, 3) | X position | Y position | Z position |
|---|---|---|---|---|
| 0.000000 | 1.000000 | -1.790827 | -0.734939 | -1.479917 |
| 0.081000 | 2.000000 | -1.738146 | 0.206219 | -1.499875 |
| 0.162000 | 3.000000 | 1.188129 | 0.529663 | -1.250452 |
| 0.314000 | 1.000000 | -1.786360 | -0.725200 | -1.470874 |
| 0.395000 | 2.000000 | -1.728063 | 0.212221 | -1.502386 |
| 0.476000 | 3.000000 | 1.182650 | 0.529757 | -1.255304 |
| 0.598000 | 1.000000 | -1.791628 | -0.727510 | -1.465327 |
| 0.679000 | 2.000000 | -1.730984 | 0.210856 | -1.492422 |
| 0.700000 | 3.000000 | 1.192947 | 0.529450 | -1.257303 |
| 0.833000 | 1.000000 | -1.790004 | -0.716768 | -1.471068 |
| 0.900000 | 2.000000 | -1.732216 | 0.204493 | -1.508408 |

FIGURE 6

| Patient # | # Data points | Predictive margin (mm) | | |
|---|---|---|---|---|
| | | X (RL) | Y (AP) | Z (SI) |
| 1 | 82991 | 1.5/-1.5 | +1.7/-1.6 | +2.7/-2.9 |
| 2 | 134119 | 1.5/-3.7 | +1.5/-1.9 | +2.0/-2.8 |
| 3 | 193490 | 1.6/-1.5 | +3.8/-3.0 | +2.1/-1.7 |
| 4 | 124046 | 2.5/-2.6 | +2.2/-3.6 | +2.7/-4.0 |
| 5 | 152128 | 1.9/-2.1 | +3.8/-2.9 | +3.5/-2.1 |
| 6 | 158632 | 1.5/-1.5 | +2.9/-2.3 | +3.6/-3.5 |
| 7 | 151958 | 1.6/-1.8 | +3.5/-1.8 | +3.2/-2.7 |
| 8 | 163329 | 1.5/-1.5 | +1.5/-3.5 | +1.6/-2.1 |
| 9 | 116044 | 1.5/-1.5 | +2.5/-2.3 | +4.2/-3.0 |
| 10 | 153983 | 1.5/-1.5 | +1.5/-1.5 | +1.5/-1.5 |
| 11 | 113428 | 1.5/-1.5 | +2.8/-2.5 | +2.9/-2.5 |
| 12 | 145490 | 1.5/-1.5 | +1.5/-3.0 | +1.5/-3.4 |
| 13 | 148558 | 1.8/-1.5 | +2.6/-2.8 | +4.2/-4.6 |
| 14 | 169188 | 1.5/-.1.5 | +5.4/-5.7 | +3.8/-4.2 |
| 15 | 131639 | 1.5/-1.5 | +1.5/-2.6 | +1.5/-2.3 |
| 16 | 155101 | 1.5/-1.5 | +1.5/-3.0 | +1.8/-3.6 |
| 17 | 139928 | 1.5/-1.5 | +2.4/-1.8 | +2.9/-3.2 |
| 18 | 140472 | 2.2/-2.2 | +2.7/-2.9 | +1.5/-2.6 |
| 19 | 112560 | 1.5/-1.5 | +1.5/-1.5 | +1.5/-2.1 |
| 20 | 157525 | 1.5/-1.5 | +3.3/-2.7 | +3.1/-1.9 |
| 21 | 179851 | 1.5/-1.5 | +1.5/-2.7 | +1.7/-2.4 |
| 22 | 195328 | 1.5/-1.5 | +2.6/-3.1 | +1.7/-2.6 |
| 23 | 149568 | 1.5/-1.5 | +2.2/-2.5 | +2.4/-3.1 |
| 24 | 134548 | 1.5/-1.7 | +2.3/-1.7 | +2.9/-2.3 |

FIGURE 7

METHODS, SYSTEMS AND COMPUTER READABLE STORAGE MEDIA STORING INSTRUCTIONS FOR DETERMINING PATIENT SPECIFIC TREATMENT PLANNING MARGINS

CROSS-REFERENCE TO RELATED APPLICATION

This application claims priority to Provisional Application Ser. No. 61/700,480 filed Sep. 13, 2012, which is hereby incorporated by reference in its entirety.

BACKGROUND

Prostate cancer is one of the leading cancers diagnosed in men within the United States and is expected to affect 241,470 men of which 28,000 will die in 2012. See, e.g., Siegel R, Ward E, Brawley O, et al. Cancer statistics, 2011: the impact of eliminating socioeconomic and racial disparities on premature cancer deaths. *CA Cancer J Clin;* 61:212-236. One of the variety of treatment options includes radiation therapy.

Radiation therapy techniques include intensity modulated radiotherapy (IMRT) and image-guided radiotherapy (IGRT). Some IGRT systems, such as the Calypso system, use radio transponders implanted within the prostate. The transponders can emit a radiofrequency of about 10 Hz during radiation treatment delivery. These transponders allow the clinician to track prostate motion real time during an entire treatment session. Real time tracking data has shown that intra-fraction prostate motion can be very significant. See, e.g., Langen K M, Willoughby T R, Meeks S L, et al. Observations on real-time prostate gland motion using electromagnetic tracking. *Int J Radiat Oncol Biol Phys* 2008; 71:1084-1090. Much like the fiducial markers, these transponders are placed prior to simulation. Once the patient is positioned on the table, these transponders relay positional information real time in 3-D. This data allows the treatment to be interrupted in the event that the transponder falls outside an acceptable range.

Accuracy of the radiotherapy procedure can be limited by uncertainties in the treatment preparation and execution. A conventional way to address these uncertainties in radiotherapy is to surround the clinical target volume (CTV) with a margin to allow for setup uncertainties and movement. This margin should be as small as possible as it increases the volume of normal tissue irradiated and thereby can increase the potential for short-term and long-term side effects to the surrounding tissue. However, many of the current margin models provide generic margin ranges. The models assume that the margins are generally uniform across all patients and all related prostate motion will fall in between these margins during treatment delivery. In addition, these protocols generally do not take into account the patient specific prostate motion.

SUMMARY

Thus, there is a need for determining patient specific treatment margins based on individualized patterns of a motion of a target (e.g., a prostate).

The disclosure relates to systems, methods, and computer-readable media storing instructions for automatically determining individualized treatment planning margins for a patient. By determining treatment margins based on patient specific patterns of motion of a target of a patient, the individualized treatment margins can be smaller and more optimal.

In some embodiments, the methods may relate to a method of determining individualized treatment planning margins for a patient. In some embodiments, the method may include processing motion data of a target obtained from at least one marker for one or more periods. Each period may include a plurality of time intervals, the processing including processing the motion data to determine an isocenter for each time interval along at least one of a plurality of axes of motion. The plurality of axes may include x axis, y axis, and/or z axis. In some embodiments, the method may include determining motion prediction data for each of the at least one of the axes from the isocenters. In some embodiments, the method may include determining treatment planning margins each of the at least one of the axes axis based on the motion prediction data. The methods can be performed by a computer having a memory and a processor.

In some embodiments, the systems may relate to a system for determining individualized treatment planning margins for a patient. The system may include a motion data processor configured to process motion data of a target obtained from at least one marker for one or more periods. Each may include a plurality of time intervals. The processing may include processing the motion data to determine an isocenter for each time interval along at least one of a plurality of axes of motion. The plurality of axes may include x axis, y axis, and/or z axis. In some embodiments, the system may include a motion prediction module configured to determine motion prediction data for each of the at least one of the plurality of axes from the isocenters. In some embodiments, the system may include a margin determination module configured to determine treatment planning margins for each of the at least one of the plurality of axes based on the motion prediction data.

In some embodiments, the computer readable media may relate to a computer-readable medium storing instructions for determining individualized treatment planning margins for a patient. The instructions may include processing motion data of a target obtained from at least one marker for one or more periods. Each period may include a plurality of time intervals, the processing including processing the motion data to determine an isocenter for each time interval along at least one of a plurality of axes of motion. The plurality of axes may include x axis, y axis, and/or z axis. In some embodiments, the instructions may include determining motion prediction data for each of the atZ least one of the plurality of axes from the isocenters. In some embodiments, the instructions may include determining treatment planning margins for each of the at least one of the plurality of axes based on the motion prediction data.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

FIG. 6 shows an example of raw motion data received from an electromagnetic transponder;

FIG. 7 shows an example of planning treatment margins determined according to embodiments for a plurality of patients.

DESCRIPTION OF THE EMBODIMENTS

Figure 1:
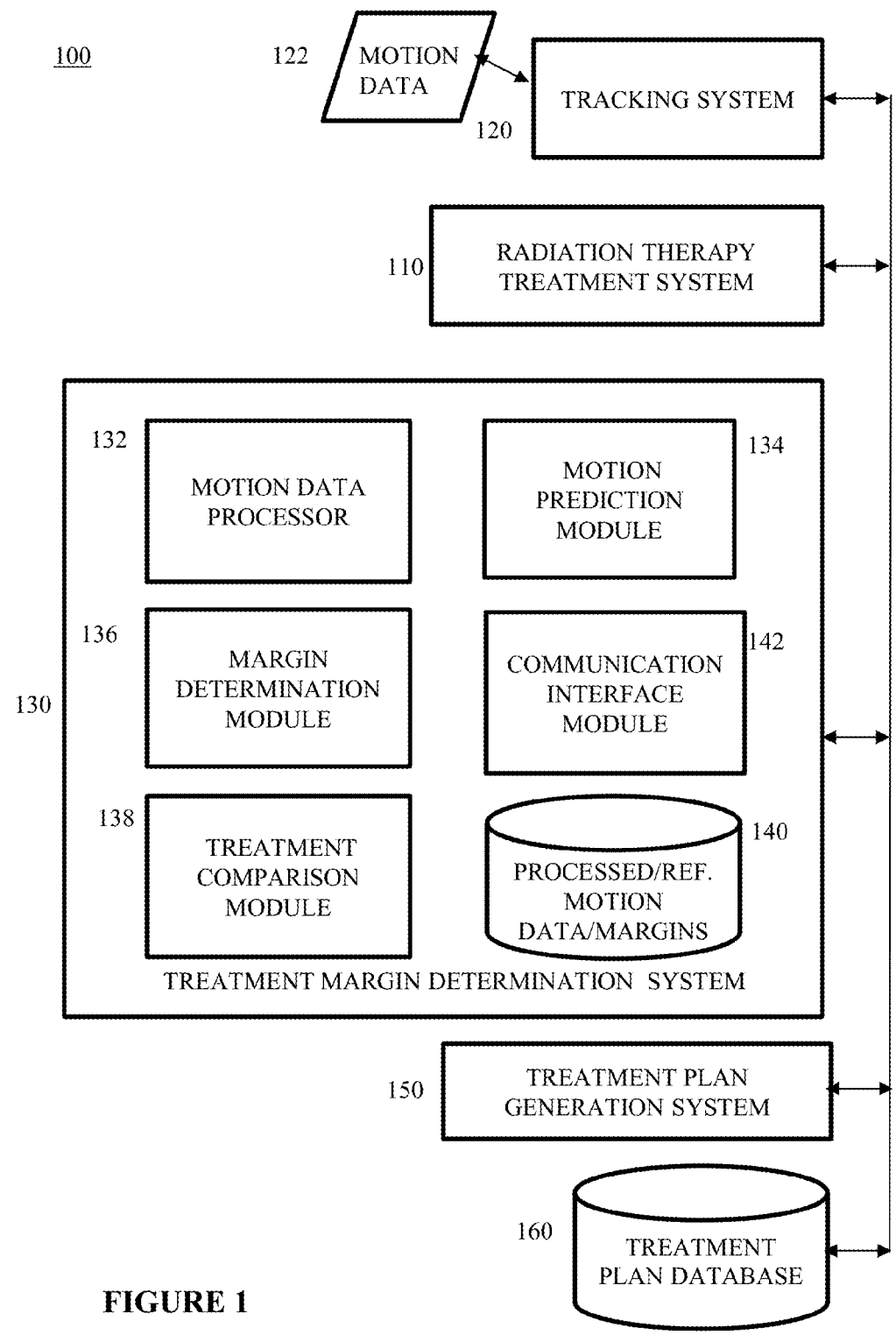
FIG. 1 shows a block diagram illustrating a system according to embodiments.

The following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosed methods, systems, and computer-readable media relate to determining individualized treatment margins. The disclosed methods, systems, and computer-readable media according to embodiments can determine individualized treatments by predicting motion of a target (e.g., an organ) in each axis based on motion data. The disclosed methods, systems, and computer-readable media according to embodiments provide a more optimal approach than conventional population based approaches. The individualized treatment margins can be smaller and more optimal because the treatment margins can incorporate patient specific patterns of motion of a target. It thus can potentially reduce dose to normal tissue and the risks of secondary cancers while maintaining acceptable doses to the target.

The disclosed methods, systems, and computer-readable media are discussed with respect to a target. The target can be an organ and/or surrounding structure, and/or a tumor within an organ and/or surrounding structure, or a combination thereof. The target is discussed with respect to the prostate. It will be understood that the target is not limited to the prostate. The disclosed methods, systems, and computer-readable media may be applied to and/or include information from other targets, such as other organs and/or regions of interests, for example, breast(s), lung(s), liver, pancreas, kidney(s), as well as other organs and/or regions.

FIG. 1 shows an example of a system 100 capable of determining individualized patient specific margins and generating a treatment plan based on the margins according to embodiments.

As shown in FIG. 1, the system 100 may include a radiation treatment system 110 configured to deliver a radiation beam to a target tissue (i.e., the tissue to be treated by the beam within the patient) and to control the delivery of the radiation. The radiation treatment system 110 may be any radiation treatment system.

In some embodiments, the system 100 may include a motion tracking system 120. The motion tracking system 120 may be any motion tracking and localization system. In some embodiments, the motion tracking system 120 may also be an imaging guidance system. The motion tracking system 120 may be configured to track in real-time a target (e.g., a prostate) relative to a machine isocenter or another external reference frame outside of the patient to determine motion data 122 during treatment planning, set up, treatment (radiation) sessions, and/or other times of the radiation therapy process. The motion tracking system 120 may be configured to obtain the motion data 122 via any suitable technique, such as by tracking one or more internal or external markers that are positioned near the target tissue. The markers may include but are not limited to electromagnetic transponders (e.g. Calypso® 4D Localization System, available from Calypso Medical Technologies of Seattle, Wash.), which can be placed internally in the patient near or within the region of interest. The coordinates of the transponders may be determined based on the radiofrequency signal emitted by the transponders.

In some embodiments, the motion data 122 (also referred to as "organ motion data") may be motion data of the target, for example, an organ included in the region of interest. The motion data 122 may be raw data. In some embodiments, the motion data 122 may include data representing motion of the target in (x, y, and/or z, and t) for a (time) period. In some embodiments, the motion data may be specific to each marker or transponder. In some embodiments, the period may correspond to at least a portion of a non-treatment planning session (e.g., pre-treatment planning or set up) and/or a treatment session (also referred to as a "fraction"). In some embodiments, one or more periods may correspond to a portion of the same session. In other embodiments, some or all of the periods may correspond to different session.

In some embodiments, the motion tracking system 120 may be any motion tracking system compatible with markers or other implanted devices. The motion tracking system 120 may include but is not limited to systems from Varian Medical Systems (e.g., Calypso), Siemens Healthcare, Accuray, RadiaDyne, Eleckta AB, as well as those developed by single modality or combinations of kV, MV, optical, MRI based tracking devices, radioactive transponders, or other systems.

In some embodiments, the markers or transponders and/or the motion tracking system 1220 may dictate the frequency at which the motion data is obtained. In some embodiments, the frequency may be about 10 Hz. In other embodiments, the frequency may be different.

In some embodiments, the system 100 may include a treatment margin determination system 130. The treatment margin determination system 130 may be configured to determine individualized treatment margins for a patient. The treatment margin determination system 130 may be configured to predict motion of the target in one or more axes of motion by determining motion prediction data based on the motion data obtained from each marker.

In some embodiments, the treatment margin determination system 130 may include a motion data processor 132 configured to process the motion data 122 received from each marker. The motion data processor 132 may be configured to process raw motion data to determine the isocenter for one or more of the axes of motion (e.g., x, y, and/or z axes) for each transponder or marker. In some embodiments, the motion data processor 132 may be configured to determine the isocenter for one or more of the axes. The x axis may correspond to the right-left motion; they axis may correspond to the anterior-posterior motion; and the z axis may correspond to the superior-inferior motion. In some embodiments, the processed motion data may include time (seconds) and right-left motion, anterior-posterior motion and/or superior-inferior motion for the isocenter for each transponder or marker.

In some embodiments, the treatment margin determination system may include a motion prediction module 134 configured to determine the motion prediction data (also referred to as "predicted motion data") from the processed image data for at least one respective axis. In some embodiments, the motion prediction module 134 may be configured to determine posterior distribution along one or more respective axes of motion. In some embodiments, the motion prediction data may be determined from the posterior distribution.

In some embodiments, the system 130 may include a (treatment planning) margin determination module 136 configured to determine treatment planning margins. The margin determination module 136 may be configured to determine individualized treatment planning margins based on the predicted motion data for the one or more axes. The margins may be used by, for example, a treatment plan generation system 150 to generate a treatment plan for a patient.

In some embodiments, the system 130 may include a treatment comparison module 138. The treatment comparison module 138 may be configured to compare real-time motion of the target during a session to the determined treatment margins. The treatment comparison module 138 may be configured to provide feedback based on intra-session image guidance. The treatment comparison module 138 may be configured to alert the practitioner when the motion of the target during a session is outside of the margins, for example, by a certain threshold.

In some embodiments, the system 130 may include a memory, for example, a database, 140 configured to store the processed motion data and/or treatment margins for each axis for one or more patients. The processed motion data may include predicted motion data and/or posterior distribution. The memory 140 may be configured to store the processed motion data and/or determined treatment margins for that patient. The memory 140 may also be configured to store a treatment margin reference that includes processed motion data and/or determined margins. In some embodiments, the treatment margin reference may be based on collected motion data for at least one patient. In some embodiments, the treatment comparison module 138 may be configured to compare the real-time motion of the target to the stored determined margins and/or processed motion data for that patient and/or to a treatment margin reference.

In some embodiments, the system 130 may include a communication interface module 142 configured to conduct receiving and transmitting of data between the modules (or systems) on the system and/or network. The communication interface module 142 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 100 may include a treatment plan generation system 150 configured to determine radiation doses to the target (e.g., prostate) and other surrounding normal structures based on the determined patient specific treatment planning margins. The treatment plan generation system 150 may be any treatment plan generation system 150. The treatment plan generation system 150, for example, may include but is not limited to Pinnacle, Eclipse, as well as others.

In some embodiments, the system 100 may include a treatment plan database 160. The treatment plan database 160 may be configured to store the treatment plans generated by the treatment plan generation system 150. The radiation therapy treatment system 110 and/or the tracking system 120 may use the treatment plan to control the treatment and/or tracking of a target (e.g., the prostate).

In some embodiments, the system 100 may include a different set of systems or modules, including additional systems or modules, including fewer systems or modules, or sets in which the functionality of the systems or modules is divided or consolidated.

In some embodiments, the modules and/or systems of the system 100 may be connected to a data network, a wireless network, or any combination thereof. In some embodiments, any of the modules and/or systems of the system 100 may be at least in part be based on cloud computing architecture. In some embodiments, the modules and/or systems may be applied to a self-hosted private cloud based architecture, a dedicated public cloud, a partner-hosted private cloud, as well as any cloud based computing architecture.

Figure 2:
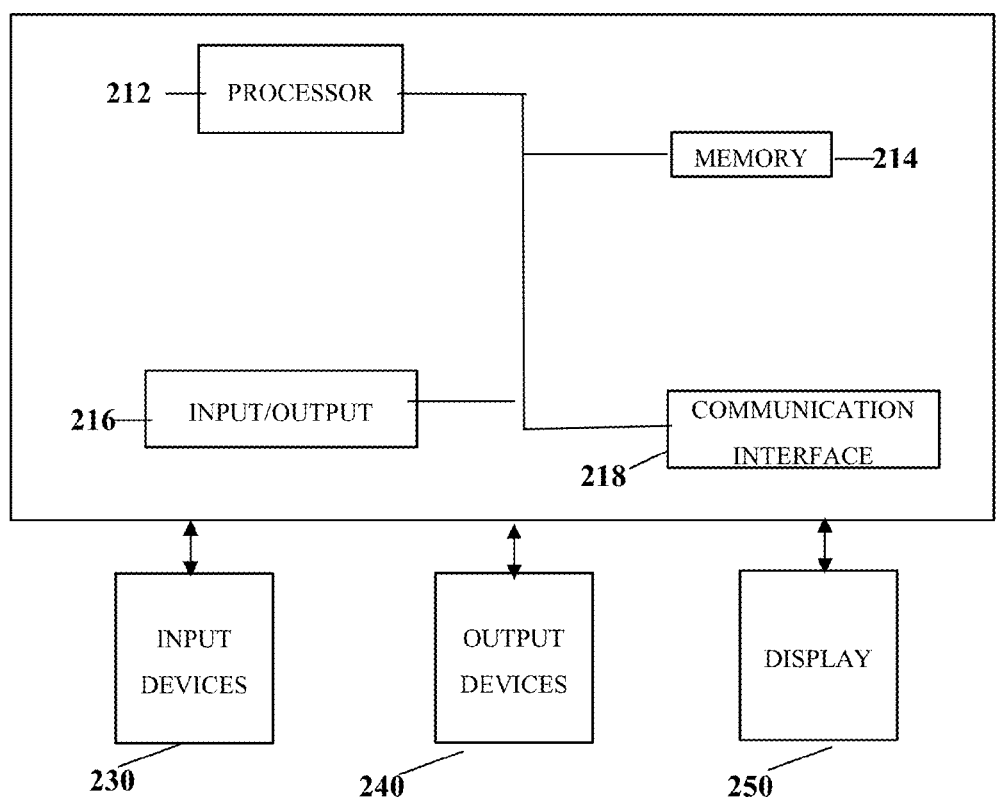
FIG. 2 shows a block diagram illustrating an example of a computing system.

One or more of the modules and/or systems of system 100 may be and/or include a computer system and/or device. FIG. 2 is a block diagram showing a computer system 200. The modules of the computer system 200 may be included in at least some of the systems and/or modules, as well as other devices of system 100.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 200 may be a computing system, such as a workstation, computer, or the like. The system 200 may include one or more processors 212. The processor(s) 212 (also referred to as central processing units, or CPUs) may be any known central processing unit, a processor, or a microprocessor. The CPU 212 may be coupled directly or indirectly to one or more computer—readable storage media (e.g., memory) 214. The memory 214 may include random access memory (RAM), read only memory (ROM), disk drive, tape drive, etc., or a combinations thereof. The memory 214 may be configured to store programs and data, including data structures. In some embodiments, the memory 214 may also include a frame buffer for storing data arrays.

The CPU 212 may be configured to determine individualized treatment margins. In some embodiments, the CPU 212 may be capable of performing the data processing and/or generation of treatment plan. In other embodiments, the system may include a separate CPU for performing the data processing and/or generation of treatment plan.

In some embodiments, another computer system may assume the data analysis or other functions of the CPU 212. In response to commands received from the input device, the programs or data stored in the memory 214 may be archived in long term storage or may be further processed by the processor and presented on a display.

In some embodiments, the system 210 may include a communication interface 218 configured to conduct receiving and transmitting of data between other modules on the system and/or network. The communication interface 218 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 210 may include an input/output interface 216 configured for receiving information from one or more input devices 230 (e.g., a keyboard, a mouse, and the like) and/or conveying information to one or more output devices 240 (e.g., a printer, a CD writer, a DVD writer, portable flash memory, etc.). In some embodiments, the one or more input devices 230 may configured to control, for example, the generation of the margins and/or treatment plan, display of the margins and/or treatment plan on a display 250, printing of the margins and/or treatment plan by a printer interface, among other things.

Figure 3:
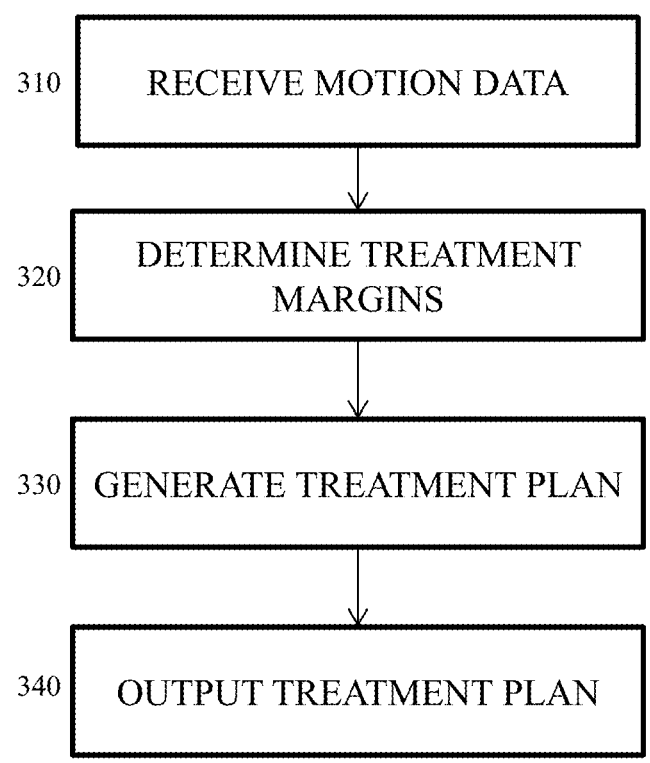
FIG. 3 shows a method of generating a treatment plan based on individualized treatment margins according to embodiments.

FIG. 3 illustrates a method 300 for determining an individualized treatment planning margins according to embodiments. In some embodiments, the method 300 may generate a radiation treatment plan based on the determined treatment planning margins. The system for carrying out the embodiments of the methods disclosed herein is not limited to the systems shown in FIGS. 1 and 2. Other systems may be used.

The methods of the disclosure are not limited to the steps described herein. The steps may be individually modified or omitted, as well as additional steps may be added. It will be also understood that at least some of the steps may be performed in parallel.

Unless stated otherwise as apparent from the following discussion, it will be appreciated that terms such as "sampling," "averaging," "combining," "comparing," "generating," "determining," "obtaining," "processing," "computing," "selecting," "receiving," "summing," "estimating," "calculating," "quantifying," "outputting," "acquiring," "analyzing," "approximating," "continuing," "resuming," "using," "halting," "alerting," "sorting," "predicting," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

As shown in FIG. 3, the method 300 may include a step 310 of receiving motion data for at least one period. The motion data may be acquired from a marker, such as an electromagnetic transponder implanted in a patient, for example, by the tracking system 120. In some embodiments, the motion data may be raw. The raw motion data may include data representing the motion of the target (prostate), in x axis (X), y axis (Y), z axis (Z), and/or time (t). The period may correspond to a non-treatment session (e.g., pre-treatment planning and/or setup) or a treatment session (e.g., a fraction (f)). In some embodiments, a period may correspond to a portion of a session. FIG. 6 shows an example of raw data obtained from an electromagnetic responder.

The motion data may include motion data for more than one marker for each period. In some embodiments, the motion data may include motion data for at least three markers for each period. In some embodiments, the motion data may include motion data for a different number of markers for each period. In some embodiments, the motion data may be received for one period. In some embodiments, the motion data may be received for more than one period. In some embodiments, the motion data may be received for at least three periods, four periods, five periods, or more than five periods.

In some embodiments, the method 320 may include a step of processing the (raw) motion data to determine treatment planning margins, for example, by the treatment margin determination system 130. The treatment planning margins may be determined for a patient based on at least the patient specific motion along one or more axes. In this way, the treatment planning margins can be individualized.

Figure 4:
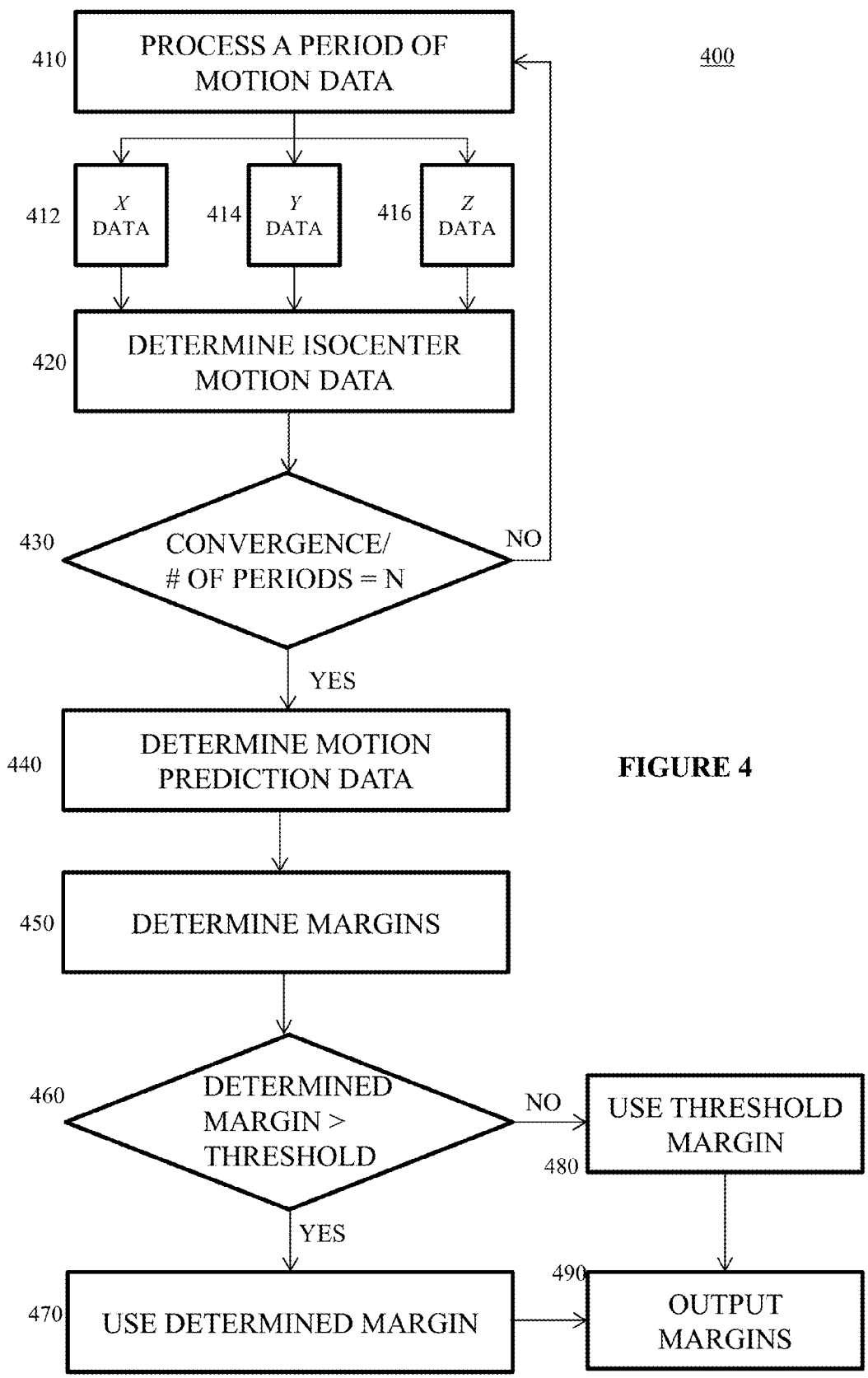
FIG. 4 shows a method of determining individualized treatment margins according to embodiments.

In some embodiments, FIG. 4 shows a method 400 according to embodiments for determining treatment planning margins for a patient. It will be understood that other methods may be used.

As shown in FIG. 4, the method 400 may include a step 410 of processing motion data for each implanted marker for a period. The motion data may be processed, for example, into a user friendly format for further analysis. In some embodiments, the data may be processed to determine for each transponder or marker and for a given period (f): $T_i$ ($t_f$, $X_f$, $Y_f$, $Z_f$). $t_f$ may correspond to total time in seconds (e.g., at 10 Hz frequency) for period, f. $t_f$ may be determined by the period, f, divided by the frequency. $X_f$ may correspond to the isocenter position in right-left direction for period, f; $Y_f$ may correspond to isocenter position in anterior-posterior direction for period, f; $Z_f$ may correspond to isocenter position in superior-inferior direction for period, f; i may correspond to the number of markers or transponders (e.g., for 3 transponders i=1 to 3); f may correspond to the period.

FIG. 4 illustrates that the data is processed for each of the axes. However, it will be understood that the data may not be processed for all of the axes. The data may be processed in one or two of the axes (at least one of the axes). In some embodiments, the axes processed may be dependent on the target. For example, some targets may have substantially limited motion in one or more of the axes.

After the data is processed into at least one of x, y, and/or z axes (steps 412, 414, and 416, respectively), the data may be separately processed (e.g., steps 420-480) for one or more of these axes to determine margins for right-left, anterior-posterior, and/or superior-inferior motion, respectively. In some embodiments, the data for more than one axis may be separately performed in parallel.

As shown in FIG. 4, the method 400 may include a step 420 of determining isocenter motion data of a target (also referred to as "organ isocenter motion data" or "target organ isocenter motion data") for at least one axis for that period (f), for example, by the motion data processor 132. The isocenter motion data for each axis may include center of mass data for each time interval ($t_i$) of that period. The time interval ($t_i$) may correspond to the time interval at which the markers measure the position of the target. The number of time intervals ($t_i$) in each time period may be based on the frequency associated with the motion data obtained. The data received from all markers or transponders for that period may be combined (e.g., averaged) to determine the center of mass (i.e., isocenter motion data). The isocenter of a target from all markers or transponders for each time interval of the period may correspond to $COM_x$, $COM_y$, and/or $COM_z$, $COM_x$, $COM_y$, and $COM_z$ corresponds to the average of the position in x, y, and z axes, respectively, for each transponder or marker for that time interval of that period. The equation for determining the isocenter of a target for the respective axis may be determined based on the following:

$$COM_x = (X_1 + X_2 + X_3)/3$$

$$COM_y = (Y_1 + Y_2 + Y_3)/3$$

$$COM_z = (Z_1 + Z_2 + Z_3)/3 \quad (1)$$

This equation (1) is based on 3 transponders or markers. However, it will be understood that more or less transponders or markers may be used and that the equation may be modified accordingly.

In some embodiments, the method 400 may include a step 430 of determining whether additional period(s) of motion data is necessary. In some embodiments, the step 430 may determine whether the processed isocenter motion data converges. In other embodiments, the step 430 may determine whether a certain number of different periods of motion data have been received and processed. In some embodiments, the number of periods may correspond to more than one period. In some embodiments, the number of periods may correspond to at least three periods. In other embodiments, the number of periods may correspond to more than three periods. In some embodiments, the number of periods may correspond to four periods, five periods, or more than five periods.

If additional periods of motion data are determined to be necessary (NO at step 430), additional motion data from each transponder or marker for a different period may be obtained and steps (410-430) may be repeated until the data converges and/or the number of periods of motion data received equals N (YES at step 430). In some embodiments, the period(s) may correspond to the same and/or different sessions. In some embodiments, the period(s) may correspond to sequential sessions.

In some embodiments, at least one of the periods may correspond to a non-treatment session, for example, an initial pre-treatment set up for plan verification. In some embodiments, one of the periods may correspond to a non-treatment session. In some embodiments, more than one period more correspond to a non-treatment session.

In some embodiments, one or more periods of motion data may have been obtained during a treatment session (e.g., fraction). In some embodiments, the first motion data may have been obtained during a non-treatment session and the subsequent motion data (e.g., second-fifth) may have obtained during subsequent treatment sessions (fractions). In some embodiments, the treatment sessions may be based on a treatment plan generated according to standard margins and/or a treatment plan generated according to embodiments.

In some embodiments, the method 400 may include a step 440 of determining predicted motion data (also referred to as "motion prediction data") along its respective axis, for example, by the motion prediction module 134. In some embodiments, the predicted motion data for an axis may be determined based on the processed motion data (e.g., isocenter motion data) for that axis. In some embodiments, the predicted motion data may correspond to the probability that the target may be disposed at a position (e.g., a $x_i$ position) along an axis during any time interval of a (e.g., future) period(s).

In some embodiments, the predicted motion data may be determined using posterior distribution. In some embodiments, the posterior distribution may be determined using a Bayesian framework. In other embodiments, the posterior distribution may be determined according to a different framework.

The determination of the posterior distribution is described with respect to the x axis, as an example. This step relates to determining posterior distribution for any axis. The following can be repeated for any of the other axes (e.g., y axis and/or z axis) or performed for any axis so that the posterior distribution can be individually determined for any of the axes.

In some embodiments, the posterior distribution (P (A/B)$_x$) may be determined using the following equation:

$$P(A/B)_x = \frac{P(B/A)_x P(A)_x}{P(B)_x} \quad (2)$$

In some embodiments, the mean ($\mu$) may be determined. For example, the mean ($\mu$) may be determined for a total of "$\eta$" target motion positions of the target (e.g., prostate) in the x axis over the number of periods. "$\eta$" target (e.g., prostate) motion positions may correspond to the total number of time intervals included in all periods. "$x_i$" represents a position of the target (e.g., prostate) in three dimensional space for a given time interval ($t_j$) as measured by the marker(s) and/or the tracking module 120. In some embodiments, there are a total number of "$\eta$" positions that have been measured at a given time interval, i, in the period. The mean may be determined using the following equation:

$$\mu_x = \frac{1}{n} \sum_{i=1}^{n} (x_i) \quad (3)$$

In some embodiments, the standard deviation (σ) may be determined. For example, the (σ) for a total of "η" motion positions of the target in the x axis over the number of periods may be determined using the following:

$$\sigma = \sqrt{\frac{1}{n}\sum_{i=1}^{n}(x_i - \mu_x)^2} \quad (4)$$

In some embodiments, the likelihood probabilities $P(B/A)_x$ may be determined. The $P(B/A)_x$ may be determined using a likelihood function. In some embodiments, $P(B/A)_x$ may be determined using the following equation:

$$P(B/A)_{x_i} = \frac{1}{\sigma_x\sqrt{2\pi}} e^{\frac{-(x_i-\mu_x)^2}{2\sigma_x^2}} \quad (5)$$

In some embodiments, the likelihood probability ($P(B/A)_x$) may be determined for all x positions ($x_i$) that were measured during the periods for a total of "η" positions. For example, i.e., the probability $P(B/A)_x$ may be determined for each of the $x_1, x_2, x_3 \ldots x_i \ldots x_n$.

In other embodiments, the likelihood probability may be determined for each x position ($x_i$) using a different function.

$P(A)_x$ corresponds to the prior information probability distribution of the events that occur during the periods. In some embodiments, $P(A)_x=1$, for example, for a uniform prior. If the $P(A)_x=1$, then the posterior distribution corresponds to the likelihood probability. In other embodiments, $P(A)_x$ may be an informed prior and may be determined from the processed motion data.

$P(B)_x$ is a scaling factor. In some embodiments, $P(B)_x=1$. In other embodiments, $P(B)_x$ may correspond to other values.

After determining the posterior distribution for the one or more axes, the treatment planning margins may be determined (step 450), for example, by the margin determination module 136. The treatment planning margins may be individually determined for each axis.

The determining step 450 is described with respect to the x axis for exemplary purposes only. The following can be repeated for any of the other axes (e.g., y axis and/or z axis) or performed for any axis so that the margins can be individually determined based on respective motion data.

In some embodiments, the treatment margins may be determined by using the $x_i$ measurements. In some embodiments, the determining step 450 may include sorting each $x_i$ measurement from the smallest to the largest x-value (i.e. −x to +x), where −x represents the largest motion the target (e.g., prostate) moved in left direction and +x represents the greatest movement the target (e.g., prostate) moved in the right direction. Each position $x_i$ can have an associated likelihood probability $P(B/A)_x$ determined in equation (5).

In some embodiments, for each axis, the treatment planning margins for each motion or axis may include determining a range of the $x_i$ measurements that include a percentage threshold of the predicted motion data along the corresponding axis. For example, the range may correspond to a small to a large value on the axis (e.g., from about −X to +X). In some embodiments, the treatment margins may correspond to the area under a histogram of the associated posterior probability that includes the percentage threshold of the $x_i$ measurements. The percentage threshold may include a value in the range from about 90%-99.9%. In some embodiments, the percentage may be about 95%. In other embodiments, the percentage may be about 99%. In other embodiments, the percentage threshold may be a different value.

In other embodiments, the treatment margins may be determined by using the mean (μ) and standard deviation (σ) of the sorted measurements and corresponding probabilities, for example, determined in equations (3) and (4), respectively. Next, the margins may be determined by using the sorted probabilities and standard deviation and multiplying it by a multiplier corresponding to the percentage threshold. The multiplier may include a value in the range from about 1.0-4.0. For example, for a threshold percentage of about 99.7%, the multiplier may be about 3.0. For a threshold percentage of about 95%, the multiplier may about be 2.0. In other embodiments, the multiplier may be a different value.

After the margin is determined, the margins for each axis may be compared to a threshold margin (step 460). In some embodiments, the threshold margin may be predetermined. In some embodiments, the threshold margin may be about ±1.5 mm. In other embodiments, the threshold margin may have a different value. In some embodiments, each axis may have a different threshold margin. In some embodiments, the threshold may be dynamic and/or according to the target. If the determined margin is above the threshold margin (YES at step 460), the determined margin may be used (step 470) and outputted (step 490). If the margin is below the threshold margin (NO at step 460), that threshold value may replace the determined margin (step 480) for that axis and may be outputted as a margin for that axis (step 490).

In some embodiments, for any of axes for which predicted motion data was not determined, the threshold margin may be outputted for that axis. In some embodiments, the threshold margin may be specific to the axis and/or target.

In some embodiments, the margin values may be outputted. In some embodiments, the outputting may include but is not limited to displaying the margins, printing the margins, and storing the margins remotely or locally, e.g., in memory 140. In other embodiments, the margins may be forwarded for further processing. In some embodiments, the method may further include transmitting the margins to another system, for example, the treatment plan generation system 150, to generate a treatment plan.

Figure 8:
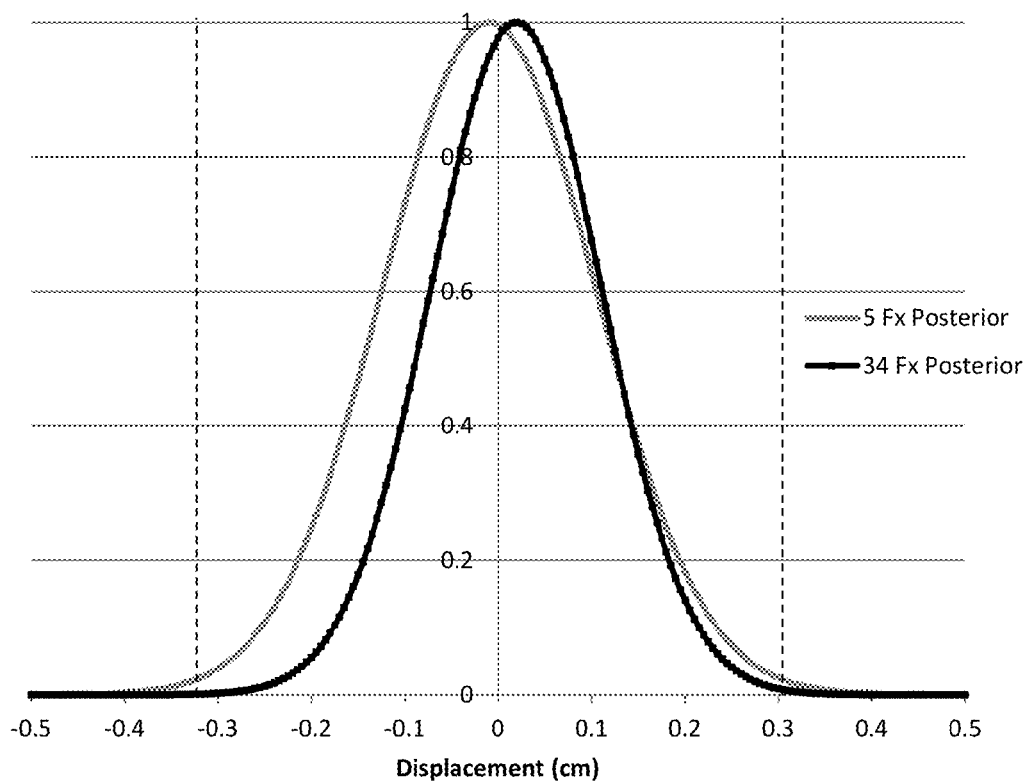
FIG. 8 shows an example of a comparison a predicted motion data along an axis of motion of a prostate determined by posterior distribution and processed actual motion data.

FIG. 7 shows an example of determined patient specific margins for a plurality of patients. FIG. 8 shows an example of a comparison of motion prediction data along an axis of motion (e.g., x, y, and/or x) of a prostate determined by posterior distribution and the posterior distribution of the collected data. The light grey line represents predicted motion data determined from prostate motion data during the first five periods. The light grey line provides that the probability of the prostate being disposed at a displacement of 1 mm from the isocenter along the given axis is about 80% for any time interval during a period. Similarly, the prostate being disposed at a displacement of 2 mm from the isocenter along the given axis is about 20%.

In some embodiments, the predicted margins may be determined the area under the grey curve (e.g., the predicted motion data) provided in a percentage threshold. For example, if the threshold is about 99%, the margin would be around +/−3.2 mm.

The black curve represents the posterior distribution of the collected motion data. The collected motion data represents the actual motion of the prostate over thirty four periods. As demonstrated in the comparison, the actual motion of the prostate occurred within the margins (range of +/−3.2 mm) determined by the predicted motion data for that patient along the axis.

In some embodiments, the method 300 may include a step 330 of generating a treatment plan based on the determined treatment margins, for example, by the treatment plan generation system 150. In some embodiments, the step 330 may be according to any known methods. In some embodiments, the step 330 may include determining radiation doses to the target and other surrounding normal structures based on the determined patient specific treatment planning margins.

In some embodiments, the method may include a step 340 of outputting the treatment plan. In some embodiments, the outputting may include but is not limited to displaying the plan, printing the plan, and storing the treatment plan remotely or locally, e.g., in memory 160. In other embodiments, the treatment plan may be forwarded for further processing. In some embodiments, the method may further include transmitting the margins to another system, for example, the radiation therapy treatment system 110 and/or tracking system 120.

Figure 5:
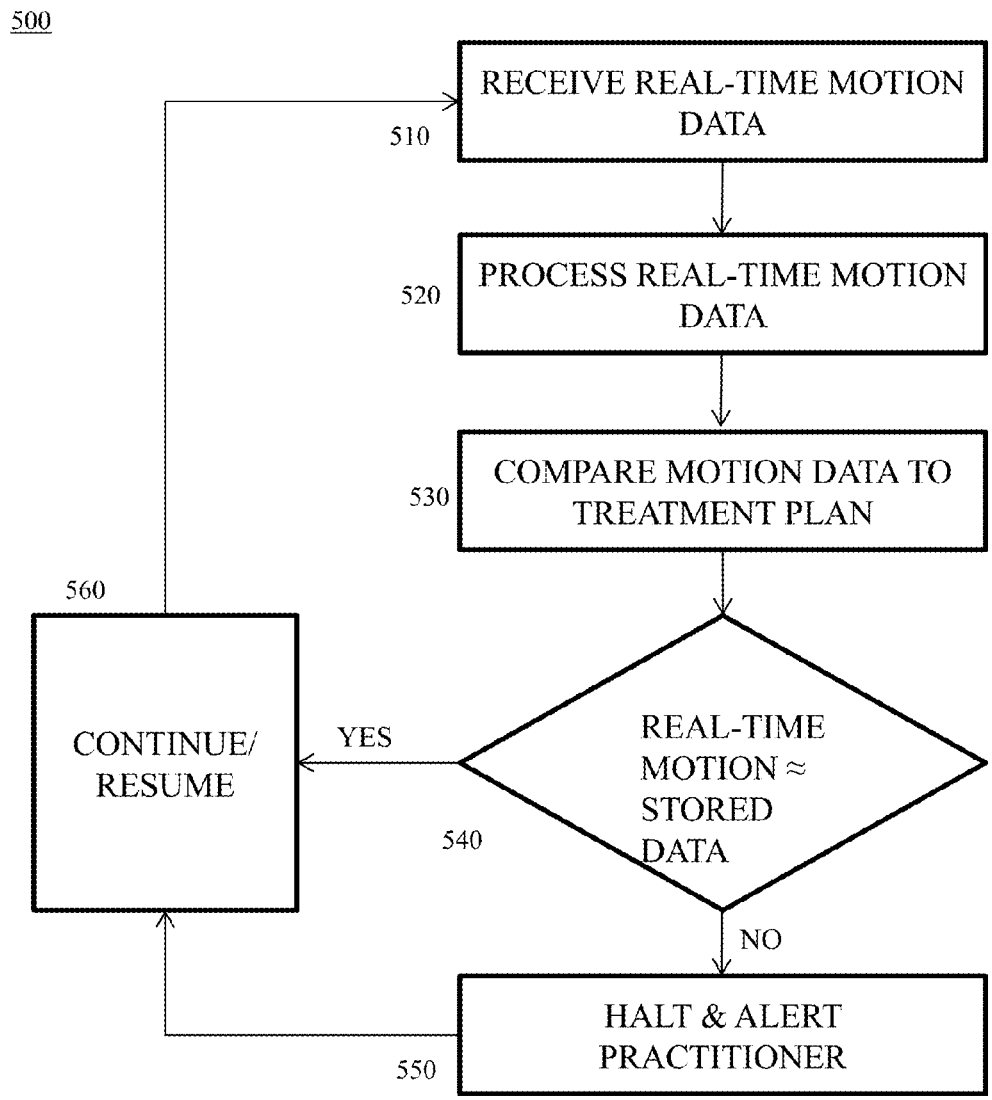
FIG. 5 shows a method of real-time monitoring of a session according to embodiments.

In some embodiments, the determined treatment planning margins may be used to provide feedback during a session, for example, a radiation treatment session and/or a non-treatment session, by, for example, the system 130. FIG. 5 shows a method 500 of providing feedback during the radiation treatment based on the determined treatment planning margins. As shown in FIG. 5, the method 500 may include a step 510 of receiving motion data of a target (e.g., prostate) in real-time from one or more markers and/or image guidance during a session.

The motion data may be raw motion data. In some embodiments, the motion data may be processed (step 520). The motion data may be processed, for example, according to steps 410-420, for example, by the motion data processor 132, to determine isocenter motion data of the target for each axis.

Next, the method 500 may include a step 530 of comparing the real-time motion data to the stored treatment planning margins and/or the corresponding stored predicted motion data, for example, by the treatment comparison module 138. In some embodiments, the treatment planning margins and/or predicted motion data may be stored in the memory 140 and/or treatment plan database. In some embodiments, the stored treatment planning margins and/or posterior distribution may include the treatment planning margins and/or predicted motion data determined for the patient based on the motion data. In other embodiments, the stored treatment planning margins and/or predicted motion data may be from a reference treatment planning margins and/or predicted motion data.

If it is determined that the real-time motion data representing motion of the target is outside of the stored margins and/or the predicted motion by a threshold (NO at step 540), then the practitioner may be alerted and/or treatment may be halted. The threshold may depend on clinical circumstances and the comparison. For example, the threshold for the margins may be about 1 or 2 mm. In some embodiments, the threshold for the predicted motion data may relate to a threshold for the posterior distribution. The threshold, for example, may be about 10% of the area under the posterior distribution. The thresholds for margins and the predicted motion are not limited to these values and may be any value.

The motion data may be outside the range due to errors, for example, resulting from human errors (e.g., positioning errors, wrong patient, etc.), treatment planning and/or treatment execution errors, among others. The treatment may resume (step 560) after the errors have been addressed. If the motion data is within the range (YES at step 540), the treatment and/or imaging may continue (step 560). The monitoring (e.g., steps 510-540) of the motion data may be repeated over at least a portion of the session. For example, the monitoring may be terminated at a point and/or the end of a session.

It is to be understood that the embodiments of the disclosure may be implemented in various forms of hardware, software, firmware, special purpose processes, or a combination thereof. In one embodiment, the disclosure may be implemented in software as an application program tangible embodied on a computer readable program storage device. The application program may be uploaded to, and executed by, a machine comprising any suitable architecture. The system and method of the present disclosure may be implemented in the form of a software application running on a computer system, for example, a mainframe, personal computer (PC), handheld computer, server, etc. The software application may be stored on a recording media locally accessible by the computer system and accessible via a hard wired or wireless connection to a network, for example, a local area network, or the Internet.

In some embodiments, the disclosed methods (e.g., FIGS. 3-5) may be implemented using software applications that are stored in a memory and executed by a processor (e.g., CPU) provided on the system 100. In some embodiments, the disclosed methods may be implanted using software applications that are stored in memories and executed by CPUs distributed across the system 100. As such, any of the systems and/or modules of the system 100 may be a general purpose computer system, such as system 200, that becomes a specific purpose computer system when executing the routine of the disclosure. The systems and/or modules of the system 100 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 1 and 2.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method of determining individualized treatment planning margins for a patient, comprising:
processing motion data of a target of a patient obtained from at least one marker for one or more periods to determine one or more isocenters of the target, each period of the one or more periods including a plurality of time intervals, the one or more isocenters including an isocenter of the target along at least one of a plurality of axes of motion for each time interval;
determining a posterior distribution for each of the at least one of the plurality of axes from the one or more isocenters;
determining motion prediction data of the target for each of the at least one of the plurality of axes from the posterior distribution;
determining treatment planning margins for each of the at least one of the plurality of axes based on the motion prediction data; and
controlling delivery of a radiation treatment to the target using the treatment planning margins.

2. The method according to claim 1, further comprising: generating a treatment plan based on the treatment planning margins.

3. The method according to claim 1, wherein:
the treatment planning margins include margins at least one of a right-left motion, an anterior-posterior motion, or a superior-inferior motion;
the plurality of axes include x axis, y axis, and z axis; and
the x axis corresponds to the right-left motion, the y axis corresponds to the anterior-posterior motion, and the z axis corresponds to the superior-inferior motion.

4. The method according to claim 3, wherein:
the at least one marker is an electromagnetic transponder.

5. The method according to claim 3, wherein:
the determining the treatment planning margins include determining a range of measurements that include a percentage threshold of the motion prediction data along each corresponding axis of the at least one of the plurality of axes, each measurement representing a position of the target along the corresponding axis.

6. The method according to claim 5, wherein the percentage threshold includes a value provided in a range of about 95%-99.9%.

7. The method according to claim 1, further comprising:
comparing the treatment planning margins for each of the at least one of the plurality of axes to a threshold;
outputting the treatment planning margins for the least one of the plurality of axes if the treatment planning margins are above the threshold; and
outputting the threshold for the treatment planning margins for the at least one of the plurality of axes if the treatment planning margins are below the threshold.

8. The method according to claim 1, wherein:
the one or more periods includes at least one of a period corresponding to at least a portion of a non-treatment session or a period corresponding to at least a portion of a treatment session.

9. The method according to claim 1, wherein the motion prediction data corresponds to a probability that the target is disposed at a position along at least one of the plurality of axes at each time interval.

10. The method according to claim 1, further comprising:
determining real-time motion data of the target;
comparing real-time motion data of the target to the treatment planning margins and/or the motion prediction data; and
controlling the delivery of the radiation treatment to the target based on the comparing.

11. A system for determining individualized treatment planning margins for a patient, comprising:
a memory; and
at least one processor, wherein the processor is configured to:
process motion data of a target of a patient obtained from at least one marker for one or more periods to determine one or more isocenters of the target, each period of the one or more periods including a plurality of time intervals, the one or more isocenters including an isocenter of the target along at least one of a plurality of axes of motion for each time interval;
determine a posterior distribution for each of the at least one of the plurality of axes from the one or more isocenters;
determine motion prediction data for the target for each of the at least one of the plurality of axes from posterior distribution;
determine treatment planning margins for each of the at least one of the plurality of axes based on the motion prediction data; and
control delivery of a radiation treatment to the target using the treatment planning margins.

12. The system according to claim 11, wherein:
the treatment planning margins include margins for at least one of right-left motion, an anterior-posterior motion, or a superior-inferior motion;
the plurality of axes include the x axis, the y axis, and the z axis; and
the x axis corresponds to the right-left motion, the y axis corresponds to the anterior-posterior motion, and the z axis corresponds to the superior-inferior motion.

13. The system according to claim 12, wherein:
the at least one marker is an electromagnetic transponder.

14. The system according to claim 12, wherein the processor is further configured to:
determine the treatment planning margins by determining a range of measurements that include a percentage threshold of the motion prediction data along each corresponding axis of the at least one of the plurality of axes, each measurement representing a position of the target along the corresponding axis.

15. The system according to claim 14, wherein the percentage threshold includes a value provided in a range of about 95%-99.9%.

16. The system according to claim 11, wherein the processor is further configured to:
compare the treatment planning margins for each of the at least one of the plurality of axes to a threshold;
output the treatment planning margins for the at least one of the plurality of axes if the treatment planning margins are above the threshold; and
output the threshold for the treatment planning margins the at least one of the plurality of axes if the treatment planning margins are below the threshold.

17. The system according to claim 11, wherein:
the one or more periods include at least one of a period corresponding to at least a portion of a non-treatment session or a period corresponding to at least a portion of a treatment session.

18. The system according to claim 11, wherein the processor is further configured to:
generate a treatment plan based on the treatment planning margins.

19. The system according to claim 11, wherein the motion prediction data corresponds to a probability that the target is disposed at a position along at least one of the plurality of axes at each time interval.

20. The system according to claim 11, wherein the processor is further configured to:
determine real-time motion data of the target;
compare real-time motion data of the target to the treatment planning margins and/or the motion prediction data; and
controlling the delivery of the radiation treatment to the target based on the comparison.

21. A non-transitory computer-readable storage medium storing instructions for determining individualized treatment planning margins for a patient, the instructions comprising:
processing motion data of a target of a patient obtained from at least one marker for one or more periods to determine one or more isocenters of the target, each period of the one or more periods including a plurality of time intervals, the one or more isocenters including an isocenter of the target along at least one of a plurality of axes of motion for each time interval;
determining a posterior distribution for each of the at least one of the plurality of axes from the one or more isocenters;
determining motion prediction data for the target for each of the at least one of the plurality of axes from the posterior distribution;
determining treatment planning margins for each axis based on the motion prediction data; and
controlling delivery of a radiation treatment to the target using the treatment planning margins.

22. The medium according to claim 21, wherein:
the determining the treatment planning margins include determining a range of measurements that include a percentage threshold of the motion prediction data along each corresponding axis, the measurements representing a position of the target.

23. The medium according to claim 21, the instructions further comprising:
determining real-time motion data of the target;
comparing real-time motion data of the target to the treatment planning margins and/or the motion prediction data; and
controlling the delivery of the radiation treatment to the target based on the comparing.

* * * * *